United States Patent [19]

Khoobiar

[11] Patent Number: 4,766,266

[45] Date of Patent: Aug. 23, 1988

[54] DEHYDROGENATION OF ISOBUTANE

[75] Inventor: Sargis Khoobiar, Kinnelon, N.J.

[73] Assignee: Arco Chemical Company, Newtown Square, Pa.

[21] Appl. No.: 797,559

[22] Filed: Nov. 13, 1985

[51] Int. Cl.$^4$ .............................................. C07C 5/333
[52] U.S. Cl. ..................... 585/660; 585/654; 585/659
[58] Field of Search ..................... 585/654, 660, 659

[56] References Cited

U.S. PATENT DOCUMENTS

| | | | |
|---|---|---|---|
| 3,470,262 | 9/1969 | Michaels et al. | 585/660 |
| 3,641,182 | 2/1972 | Box et al. | 585/660 |
| 3,864,284 | 2/1975 | Clippinger et al. | 502/334 |
| 3,915,845 | 10/1975 | Antos | 502/230 |
| 4,172,853 | 10/1979 | Antos | 585/660 |
| 4,366,091 | 12/1982 | Antos | 502/310 |
| 4,430,517 | 2/1984 | Imai et al. | 585/660 |
| 4,513,162 | 4/1985 | Al-Muddarris | 585/654 |
| 4,532,365 | 7/1985 | Khoobiar | 585/629 |
| 4,542,248 | 9/1985 | Lucien | 585/660 |
| 4,551,574 | 11/1985 | Imai et al. | 585/660 |

*Primary Examiner*—Asok Pal
*Attorney, Agent, or Firm*—Harold N. Wells

[57] ABSTRACT

Isobutane is dehydrogenated to isobutylene with minimal, preferably no more than 15%, loss of the fresh feed isobutane by structural isomerization or cracking, even when the dehydrogenation feed contains substantial amounts of isobutylene. The catalysts employed comprise platinum and promoting amounts of at least one of indium, neodymium, and tin on a nonacidic support, such as zinc aluminate. The reaction is carried out at a pressure of 0.14 to 2 bar, and an outlet temperature, °K, minimum residence time, sec., defined by the equation $$R = 1.76 \times 10^{-4} e^{7890/T}.$$

7 Claims, No Drawings

DEHYDROGENATION OF ISOBUTANE

PRIOR ART

The invention relates to the dehydrogenation of isobutane to the corresponding olefin, isobutylene, which is subsequently oxidized to methacrolein. The present invention is more particularly related to the integrated process disclosed in U.S. Pat. No. 4,532,365 for making unsaturated aldehydes, which is incorporated by reference into the present disclosure. The dehydrogenation of alkanes to their corresponding olefins is said to take place over catalysts, preferably platinum plus tin, indium, or rhenium on a support, such as zinc aluminate. The process was to be carried out with molar ratios of isobutane to steam between 1/1 and 1/10 and at 400°-700° C. and relatively low pressures up to about 10 kg/cm² gauge.

It has now been recognized that, since the recycle gases in such a process contain substantial amounts of isobutylene, it is essential—if such a process is to be operated economically—that the structural isomerization of isobutane or isobutylene to the normal form be minimized, since the less valuable straight-chain hydrocarbons represent a loss of feedstock. As Example 7 of U.S. Pat. No. 4,532,365 shows, the feed to dehydrogenation may include about 30% isobutylene which was not converted to methacrolein in a downstream oxidation reactor. If significant isomerization of either isobutane or isobutylene should occur, then the cost of operating such an integrated process is increased, as opposed to a once-through process, and offsetting the inherent advantages of the integrated process disclosed in U.S. Pat. No. 4,532,365.

Many of the patents disclosing processes for dehydrogenation of alkanes do not discuss the isomerization of the feed material. However, there are some which do so. U.S. Pat. No. 3,470,262 discloses a process which uses a platinum-chromium catalyst supported on zinc aluminate and is said to minimize isomerization by adding alkali metal oxides. It was suggested that various inert diluents could be used, preferably nitrogen, hydrogen, or methane.

U.S. Pat. No. 3,641,182 is similar, but discloses a process in which platinum and tin are supported on a zinc aluminate spinel and which optionally adds alkali metals. The process differs in that it uses steam as a diluent and features high-temperature calcination of the support. Isomerization of the feedstock is not discussed.

In U.S. Pat. No. 3,864,284 the ratio of tin to platinum is shown to be critical to obtaining a high selectivity to isobutylene from isobutane. A nonacidic support is used, but spinels such as zinc aluminate are not mentioned. Hydrogen is used as a diluent.

Hydrogen is also used as a diluent in U.S. Pat. No. 4,366,091. The catalyst is platinum-tin combined with rhenium-carbonyl on a support, which may be a spinel. Alkalis or alkaline earths are added to ensure that the catalyst is nonacidic and are said to minimize side reactions including skeletal isomerization.

An earlier patent commonly assigned with U.S. Pat. No. 4,366,091 is U.S. Pat. No. 3,915,845, which disclosed a platinum-Group IV (e.g., tin)-neodymium supported catalyst which was usually acidic. However, where it was to be used for dehydrogenation, an alkali or alkaline earth was to be included, and the halogen content was to be kept as low as possible.

Halogen content was increased in U.S. Pat. No. 4,430,517 to improve activity and selectivity of platinum-Group IV-alkali/alkaline earth supported catalysts. Again, hydrogen was used as a diluent.

Recent U.S. Pat. No. 4,513,162 discloses a dehydrogenation process, especially for isobutane, in which isomerization is said to be avoided by using catalysts which do not contain Group VIII metals. Base metal oxide catalysts are preferred to minimize isomerization of, for example, isobutane to n-butane or isobutylene to n-butene.

It has now been found that, in a dehydrogenation process where the feed includes substantial amounts of the product olefin, it is possible to obtain good yields of product from the isoalkane feed while minimizing the production of the straight-chain (normal) form by structural isomerization, provided the conditions required by the invention are observed.

SUMMARY OF THE INVENTION

In the process disclosed in U.S. Pat. No. 4,532,365, isobutane is dehydrogenated in the presence of steam to isobutylene, after which the isobutylene in the dehydrogenation effluent, also containing unconverted isobutane along with hydrogen and steam, is oxidized to form methacrolein. After separation of the methacrolein, the unreacted isobutane and isobutylene are returned to the dehydrogenation reactor. Loss of the isobutylene which is recycled must be minimized. In the present invention, the dehydrogenation process is operated so as to limit the isomerization of isobutane or isobutylene to their corresponding straight-chain (i.e., normal) form. Preferably, no more than 15% of the fresh feed isobutane is lost by structural isomerization or cracking.

Typically, the feed gas to the dehydrogenation reactor may contain 20 to 40 mol % isobutane and 3 to 15 mol % isobutylene and 15 to 40 mol % steam. By avoiding isomerization to the straight-chain equivalents, the loss of isobutylene product is avoided, with substantial economic benefits. Accomplishing this objective requires operating within certain parameters according to the invention.

The catalyst will be selected from a group which has been found to provide a high selectivity to isobutylene, with minimum structural isomerization to the normal butenes. Preferred catalysts comprise platinum plus at least one of the group consisting of In, Nd, and Sn on a nonacidic support, preferably zinc aluminate. The reaction is carried out at a pressure of 0.14 to 2 bar and at a residence time no lower than is defined by the equation $$R = 1.76 \times 10^{-4} e^{7890/T},$$

where

R = minimum residence time for the $C_4$ portion, seconds

T = average temperature, °K., at the end of the onstream cycle.

The dehydrogenation reaction is highly endothermic; consequently, the catalyst will be supplied with heat from external sources. In preferred embodiments, heat will be supplied indirectly by heat exchangers in the catalyst bed or by tubular reactors surrounded by a heating medium. Alternatively, multiple adiabatic beds may be used with heating of the effluent of one bed before introducing it to the downstream catalyst bed. Direct heating may also be used, for example, by heating a carrier gas or a portion of the feed above the desired inlet temperature and adding the superheated fluid to the cooled effluent between the adiabatic beds.

DESCRIPTION OF THE PREFERRED EMBODIMENTS

Although it is known to dehydrogenate alkanes generally, and isobutane in particular, the application of dehydrogenation as used in U.S. Pat. No. 4,532,365 is different from processes previously known, since it is integrated with a downstream oxidation to produce methacrolein. A substantial amount of unconverted isobutylene is found in the isobutane recycled to the dehydrogenation reactor because the oxidation to methacrolein is not complete. Since isobutylene is the product of dehydrogenation, it should not be included in the feed to the dehydrogenation reactor for two reasons: first, it reduces the yield of isobutylene per pass and, second, it will be structurally isomerized, at least in part, to n-butenes. The isobutylene could be recovered from the recycle gas, leaving the isobutane to be returned to the dehydrogenation reactor. One method which might be used to remove isobutylene would have particular advantages in the integrated process for producing methacrolein from isobutane. If the isobutylene were hydrated in the presence of an acid catalyst, the resulting tertiary butanol would be a suitable feed for oxidation to methacrolein; alternatively, it could be purified and used as a gasoline additive. Reducing the isobutylene content in the dehydrogenation feed will ultimately lower the loss of fresh feed isobutane to structural isomerization and cracking, since isobutylene is more susceptible to such reactions.

The loss by isomerization of isobutylene to n-butene or isobutane to n-butane will add significant cost to the process. In U.S. Pat. No. 4,513,162 it is suggested that, if Group VIII noble metals are used to catalyze the dehydrogenations of isobutane, structural isomerization will occur. It has now been found that, even when large amounts of isobutylene are present in the feed to the dehydrogenation reactor, loss to structural isomerization or cracking can be limited to below 15%.

Accomplishing this objective has been found to require control of a combination of factors. The catalyst may contain Group VIII metals, despite the suggestion in U.S. Pat. No. 4,513,162 that they should be avoided. However, the catalyst composition should be selected to minimize the tendency to isomerize the isobutylene to n-butene or isobutane to n-butane. This generally requires proper selection of the catalytic metals and a nonacidic support, such as normally acidic materials which have been neutralized by addition of alkali metals and the like, or inherently nonacidic supports such as zinc aluminate. Preferred catalysts comprise platinum plus at least one of the group of promoters consisting of In, Nd, and Sn on zinc aluminate. The amount of platinum (or any other noble metal) will, of course, be relatively small, say, an effective amount up to about 1 weight percent. The catalysts may be prepared by various techniques familiar to those skilled in the art, particularly by impregnation of the porous support with solutions containing compounds of the catalytic metals, followed by heating to evaporate the solvents and to decompose the metal compounds. By proper formulation a catalyst can be prepared which is capable of dehydrogenation of isobutane with minimum loss to structural isomerization or cracking.

Minimizing isomerization also requires establishing reaction conditions which permit the catalyst to achieve that objective. The conditions for isobutane dehydrogenation given in U.S. Pat. No. 4,532,365 were as follows: a mol ratio of isobutane to steam between 1/1 and 1/10, an inlet temperature of 400°–700° C., and a pressure between about 2–10 kg/cm$^2$ gauge. It has now been found that, if the reaction conditions are maintained within certain limits, no more than about 15% of the fresh isobutane is lost to isomerization or cracking per pass. The reaction generally is carried out under conditions which are not governed by chemical equilibrium. Desirably, the ratio of isobutylene to isobutane will be 80% or more of the equilibrium under the reaction conditions selected. The loss of isobutylene or isobutane to the "normal" form is established by chemical reaction rate, or kinetic, considerations. Thus, it becomes possible to obtain good yields of isobutylene from isobutane while limiting losses. More specifically, the following are considered to define necessary conditions. The contact time of the gas with the catalyst should be short to avoid reaching cheimcal equilibrium. The pressure in the reactor should be 0.14 to 2 bar. Since the reaction is endothermic, the temperature drops across the catalyst bed, and the temperature of the catalyst is critical.

It has been found that, in an operation with the pressure range just given, the space velocity and temperature are interrelated and that together they determine the permissible conditions under which losses to structural isomerization and cracking, expressed as loss of fresh feed isobutane, can be kept below about 15%. The limiting conditions may be expressed by the following formula:

$$R = 1.76 \times 10^{-4} e^{7890/T},$$

where
  R=minimum residence time of C$_4$ portion, seconds
  T=average temperature, °K, at the end of an on-stream cycle.

The dehydrogenation process is to be operated at a residence time no lower than the value calculated to correspond to the average catalyst temperature selected or, alternatively, the temperature should not be higher than the value calculated from the residence time selected. Average temperature refers to the arithmatic average of the inlet and outlet temperature. The use of the term "on-stream cycle" refers to the normal manner of operating such dehydrogenation reactors. The catalysts deactivate rapidly and must be regenerated frequently, say, every 1 to 12 hours, preferably 2 to 5 hours. Consequently, the end of the "on-stream" or useful cycle is the period just before the catalyst is taken out of service temporarily for regeneration.

Another aspect of the dehydrogenation process which requires consideration is the method of supplying heat to the reactor to offset the heat absorbed by dehydrogenation of isobutane. Maintaining constant temperature in the reactor is not feasible, even in a tubular reactor where heat is supplied to the tubes containing the catalyst. Care must be taken to avoid gas temperatures above those selected. Various methods of supplying the heat of reaction may be used. Heat may be supplied indirectly by heat exchangers in the catalyst bed or by using tubular reactors. If adiabatic reactor beds are used, the effluent gases from one reactor may be reheated and returned to a downstream reactor. Alternatively, direct heating, as by using heat carrier gases, may be used.

Application of the invention is illustrated in the following example.

EXAMPLE

If the feed stream is substantially pure isobutane (i.e., it contains no isobutylene) it has been determined that, when using a Pt-Nd on zinc aluminate catalyst, a selectivity of 95% or more to isobutylene can be obtained with a residence time of about 5 seconds at a temperature of about 510° C. or lower.

If the feed stream contains about 28% isobutane plus 7% isobutylene, a 95% selectivity to isobutylene is not obtained at the same residence time over the same catalyst. That would require reducing the residence time to about 2.3 seconds at the same temperature, and the conversion of isobutane would be substantially reduced. However, it is possible to operate without losing more than 15% isobutane (i.e., 85% selectivity to isobutylene) at a residence time of about 5 seconds by maintaining the temperature at about 492° C. or lower.

One skilled in the art will recognize that the percentage conversion of isobutane is an important factor in determining the yield of isobutylene. Therefore, the catalyst and the temperature will be selected so that the conversion of isobutane to isobutylene is suitable while remaining at or below the temperature set by the invention as determining the irretrievable loss of isobutylene or isobutane to their corresponding straight-chain or "normal" forms.

What is claimed is:

1. A process for the dehydrogenation of isobutane to isobutylene in the presence of steam over a noble metal catalyst followed by oxidation of said isobutylene to methacrolein, wherein the feed gas to said dehydrogenation catalyst comprises fresh isobutane and a recycle gas comprising isobutylene derived from said oxidation of isobutylene to methacrolein, thereby providing a combined gas containing 20 to 40 mol % isobutane and 3 to 15 mol % isobutylene and 15 to 40 mol % steam, the improvement comprising isomerizing or cracking no more than 15% of the fresh isobutane in the feed gas by employing a catalyst comprising platinum plus at least one of the group consisting of In, Nd, and Sn on a nonacidic support, and carrying out said dehydrogenation at a pressure of 0.14 to 2 bar and at a residence time no lower than that defined by the equation:

$$R = 1.76 \times 10^{-4} e^{7890/T},$$

where
R = minimum residence time for the $C_4$ portion, seconds
T = average temperature, °K, at the end of the on-stream cycle.

2. The process of claim 1 wherein said catalyst is platinum and neodymium supported on zinc aluminate.
3. The process of claim 1 wherein said catalyst is platinum and indium supported on zinc aluminate.
4. The process of claim 1 wherein said catalyst is platinum and tin supported on zinc aluminate.
5. The process of claim 1 wherein heat is supplied to the catalyst to replace the endothermic heat of reaction.
6. The process of claim 2 wherein said process is carried out in at least two adiabatic stages, with reheating between stages.
7. The process of claim 3 wherein hot gases are introduced after the temperature of the gases has been reduced by the endothermic heat of reaction.

* * * * *